(12) United States Patent
Roeder, Jr.

(10) Patent No.: US 11,638,766 B2
(45) Date of Patent: May 2, 2023

(54) FORWARD EMITTING ULTRAVIOLET HELMET

(71) Applicant: Gordon S Roeder, Jr., Quakertown, PA (US)

(72) Inventor: Gordon S Roeder, Jr., Quakertown, PA (US)

(*) Notice: Subject to any disclaimer, the term of this patent is extended or adjusted under 35 U.S.C. 154(b) by 269 days.

(21) Appl. No.: 17/113,089

(22) Filed: Dec. 6, 2020

(65) Prior Publication Data

US 2021/0299297 A1    Sep. 30, 2021

Related U.S. Application Data

(60) Provisional application No. 62/994,888, filed on Mar. 26, 2020.

(51) Int. Cl.
| | | |
|---|---|---|
| *A61L 2/10* | (2006.01) | |
| *H05B 47/115* | (2020.01) | |
| *H05B 47/16* | (2020.01) | |
| *F21V 21/084* | (2006.01) | |

(Continued)

(52) U.S. Cl.
CPC ............... *A61L 2/10* (2013.01); *A61L 2/24* (2013.01); *F21V 14/02* (2013.01); *F21V 21/084* (2013.01);

(Continued)

(58) Field of Classification Search
CPC .......... A61L 2/10; A61L 2/24; A61L 2202/11; A61L 2202/14; A61L 2202/16;

(Continued)

(56) References Cited

U.S. PATENT DOCUMENTS 5,688,039 A    11/1997  Johnson
6,340,234 B1    1/2002  Brown, Jr.

(Continued)

FOREIGN PATENT DOCUMENTS

WO    WO-2018231887 A1 * 12/2018 ............. F16M 11/10

OTHER PUBLICATIONS

Welch et al., "Far-UVC light: a new tool to control the spread of airborne-mediated microbial diseases", Feb. 2018, Scientific Reports (Year: 2018).*

*Primary Examiner* — Jennifer Wecker
*Assistant Examiner* — Brady C Pilsbury
(74) *Attorney, Agent, or Firm* — Michael J. Feigin, Esq.; Feigin and Fridman LLC (57) ABSTRACT

A headlamp for killing microorganisms on a surface is disclosed. The headlamp includes a head strap for donning the headlamp onto a head, a light source emitting ultraviolet light that sanitizes surfaces in which the ultraviolet light contacts, and an adjustment mechanism that adjusts the light source with respect to the head strap in a direction the user is looking such that the light emitted from the light source contacts said surface. A proximity sensor powers on the light source when the user is within a predetermined distance away from the surface. A timer powers off the light source when the light source has contacted the surface for predetermined amount of time. An indicator provides a que that the surface is safe to touch. A motion detector powers the light source on when motion is detected proximate thereto and powers off the light source absent motion proximate thereto.

20 Claims, 7 Drawing Sheets

(51) Int. Cl.
*F21V 23/04* (2006.01)
*A61L 2/24* (2006.01)
*F21V 14/02* (2006.01)

(52) U.S. Cl.
CPC ........ *F21V 23/0471* (2013.01); *H05B 47/115* (2020.01); *H05B 47/16* (2020.01); *A61L 2202/11* (2013.01); *A61L 2202/14* (2013.01); *A61L 2202/16* (2013.01)

(58) Field of Classification Search
CPC .... F21V 14/02; F21V 21/084; F21V 23/0471; H05B 47/116; H05B 47/115; Y02B 20/40
See application file for complete search history.

(56) References Cited

U.S. PATENT DOCUMENTS

| | | |
|---|---|---|
| 6,447,721 B1 | 9/2002 | Horton, III et al. |
| 6,733,150 B1 | 5/2004 | Hanley et al. |
| 8,084,752 B2 | 12/2011 | Ranta et al. |
| 9,358,313 B2 | 6/2016 | Deal |
| 9,557,106 B2 | 1/2017 | Stewart |
| 10,195,300 B2 | 2/2019 | Lloyd |
| 11,085,611 B2 * | 8/2021 | Walvekar ............... F16M 11/10 |
| 2010/0277894 A1 * | 11/2010 | Kim ...................... F21V 21/145 |
| | | 362/105 |
| 2013/0301242 A1 * | 11/2013 | Sharrah ................... F21V 5/006 |
| | | 362/105 |
| 2015/0090903 A1 * | 4/2015 | Cole ......................... A61L 2/24 |
| | | 250/492.1 |
| 2015/0217011 A1 | 8/2015 | Bettles et al. |
| 2016/0106873 A1 * | 4/2016 | Dobrinsky ................ A61L 9/00 |
| | | 250/393 |
| 2017/0216472 A1 | 8/2017 | Stibich et al. |
| 2017/0296686 A1 * | 10/2017 | Cole ......................... A61L 2/24 |
| 2020/0060359 A1 * | 2/2020 | Jascomb ............ A41D 13/1218 |
| 2020/0170092 A1 * | 5/2020 | Lange ................. F21V 33/0008 |
| 2021/0252177 A1 * | 8/2021 | LaPorte .................... A61L 2/28 |
| 2021/0290793 A1 * | 9/2021 | Tung ........................ A61L 2/26 |

\* cited by examiner

FORWARD EMITTING ULTRAVIOLET HELMET

FIELD OF THE DISCLOSED TECHNOLOGY

The disclosed technology relates generally to killing microorganisms, such as germs, viruses, bacteria, fungi, protozoa, and the like. More specifically, the present disclosed technology relates to a far-emitting ultraviolet headlamp that emits ultraviolet light at surfaces, such as railings, doorknobs, door handles, countertops, tabletops, and the like, to kill microorganism present thereon before touching the surface.

BACKGROUND

The COVID-19 pandemic has caused to date about 1.5 billion people in the world to be ordered by their governments to limit travel, stay at home, limit visitation and interaction with their families and loved ones, and limit their social activities, generally. The virus is believed to live for days or even more than a week on surfaces such as railings, doorknobs, door handles, countertops, tabletops, and the like, especially those surfaces made of stainless steel. Those who contract the virus are often asymptomatic for up to two weeks and even then, may remain asymptomatic or have a mild case confusable with the common cold. Others who contract the virus have flu-like symptoms, may develop pneumonia, or have breathing trouble which has led to hundreds of thousands of deaths and is projected to cause many more deaths in the near future.

Headlamps are a form of head gear which have a light source that emits light. Typically, headlamps have been known to be used by miners in caves and others in dark places to see in front of them while keeping their hands free for use of other tools. Indeed, headlamps may be utilized to emanate light in a direction in which the user's head is face.

Far-UVC is defined as ultraviolet light having a wavelength ranging between 200 and 280 nanometers. Far-UVC having a wavelength of 222 nanometers is believed to be most effective in killing microorganisms such as viruses or bacteria, while being safe for human eyes and skin. Far-UVC works by destroying the ribonucleic acid (RNA) and deoxyribonucleic acid (DNA) of microorganisms.

Accordingly, there is a need to for a headlamp capable of emanating far-UVC light toward a surface to help make the surface safe to touch by killing microorganisms present thereon, including viruses such as COVID-19.

SUMMARY OF THE DISCLOSED TECHNOLOGY

Disclosed herein is a far-emitting ultraviolet headlamp for donning onto a user's head to emanate ultraviolet light on surfaces to kill microorganisms, such as viruses and bacteria present thereon. The headlamp includes a head strap for mounting the headlamp circumferentially around a user's head, a light source disposed on the head strap, the light source emitting ultraviolet light having a wavelength in the range of 200 to 280 to sanitize surfaces in which the light contacts by killing the RNA and DNA of the microorganisms present on the surface, and an adjustment mechanism coupled to the light source configured to angle the light source with respect to the head strap in the direction the user's eyes are looking such that the light emitted from the light source makes contact with the surface being looked at by the user.

In embodiments, the headlamp includes a proximity sensor coupled to the light source. The proximity sensor senses the distance of a surface in the user's environment with respect to the light source. The proximity sensor powers on the light source when the proximity sensor determines the user is within a predetermined distance away from the surface.

In some embodiments, the headlamp includes a timer coupled to the light source. The timer powers off the light source when the light source has contacted a surface after a predetermined amount of time.

In other embodiments, the headlamp includes a visual indicator coupled to the light source and the timer. The visual indicator ques the user that the surface has been adequately sanitized after the predetermined amount of time has elapsed to notify the user that the surface is safe to touch. In one embodiment, the visual indicator is a colored light positioned on the head strap.

In alternative embodiments, the headlamp includes an audio indicator coupled to the light source and the timer. The audio indicator ques the user that the surface has been adequately sanitized after the predetermined amount of time has elapsed to notify the user that the surface is safe to touch.

In embodiments, the headlamp includes a motion detector coupled to the light source. The motion detector detects motion adjacent to the light source and powers on the light source when motion is detected proximate to the light source and powers off the light source absent motion proximate to the light source.

In some embodiments, the adjustment mechanism includes a mechanical swivel which pivots the light source along a vertical axis.

In certain embodiments, the adjustment mechanism includes a calibrator that angles the light source into a specific position based on the position of the light source with respect to the user's head, the length of the user's arm, and behaviometric information about the user.

In embodiments, the behaviometric information about the user includes data related to the frequency upon which the user lifts their hand to touch an object and how far away the user lifts their hand when touching the object.

In some embodiments, the light source emits ultraviolet light at a wavelength ranging from 207 to 222 nanometers. In certain embodiments, the light source emits ultraviolet light at a wavelength of 222 nanometers.

In embodiments, the headlamp includes a forehead pad for abutting the user's forehead. The forehead pad is disposed on the front end of the head strap and includes a first side and a second side opposite the first side. The head strap includes a first end and a second end opposite the first end. The first end is adjustably coupled to the first side of the forehead pad while the second end is adjustably coupled to second side of the head strap.

Also, disclosed herein is a method of killing microorganisms present on a surface with an ultraviolet light disposed on a user's head. The method includes donning an ultraviolet light source onto the user's head, positioning the ultraviolet light source on the forehead of the user's head, adjusting the ultraviolet light source to emanate ultraviolet light having a wavelength in the range of 200 to 280 nanometers in a direction away from the user's forehead, directing the ultraviolet light toward the surface, and illuminating the surface with the ultraviolet light for a predetermined amount of time.

In embodiments, the method includes powering on the ultraviolet light source in response to the ultraviolet light source being within a predetermined proximity to the surface and powering off the ultraviolet light source in response to the ultraviolet light source being outside of the predetermined proximity to the surface.

In some embodiments, the method includes powering off the ultraviolet light source after the ultraviolet light has illuminated the surface for the predetermined amount of time.

In certain embodiments, the method includes audially or visually indicating that the ultraviolet light has illuminated the surface for the predetermined amount of time to indicate when the surface has been sanitized and is safe to touch.

In other embodiments, the method includes powering on the ultraviolet light source when motion is detected within a predetermined proximity to the ultraviolet light source and powering off the ultraviolet light source absent motion within the predetermined proximity to the ultraviolet light source for a predetermined amount of time.

In some embodiments, the method includes illuminating an area directly in front of the user at an angle in the range of 5 degrees to 45 degrees with respect to a vertical axis of the user.

"Ultraviolet light" is defined as "electromagnetic radiation having a wavelength ranging from 10 to 400 nanometers." "Far-emitting ultraviolet light" also referred to as "far-UVC" is defined as "ultraviolet light not capable of penetrating mammalian skin, but capable of traversing microbes, such as microorganisms." "Microorganism" also referred to as a "microbe" is defined as "a microscopic organism, which may exist in its single-celled form or a colony of cells, such as a bacterium, virus, fungus, and protozoa."

Any device or step to a method described in this disclosure can comprise or consist of that which it is a part of, or the parts which make up the device or step. The term "and/or" is inclusive of the items which it joins linguistically and each item by itself. "Substantially" is defined as "at least 95% of the term being described" and any device or aspect of a device or method described herein can be read as "comprising" or "consisting" thereof.

DETAILED DESCRIPTION OF EMBODIMENTS OF THE DISCLOSED TECHNOLOGY

The disclosed technology provides a far-emitting ultraviolet headlamp for donning onto a user's head to emanate ultraviolet light on surfaces to kill microorganisms, such as viruses and bacteria present thereon. The headlamp includes a head strap for mounting the headlamp circumferentially around a user's head, a light source emitting ultraviolet light having a wavelength in the range of 200 to 280 to sanitize surfaces in which the light contacts by killing the RNA and DNA of the microorganisms present on the surface, and an adjustment mechanism coupled to the light source configured to angle the light source with respect to the head strap in the direction the user's eyes are looking such that the light emitted from the light source makes contact with the surface being looked at by the user.

Figure 1:
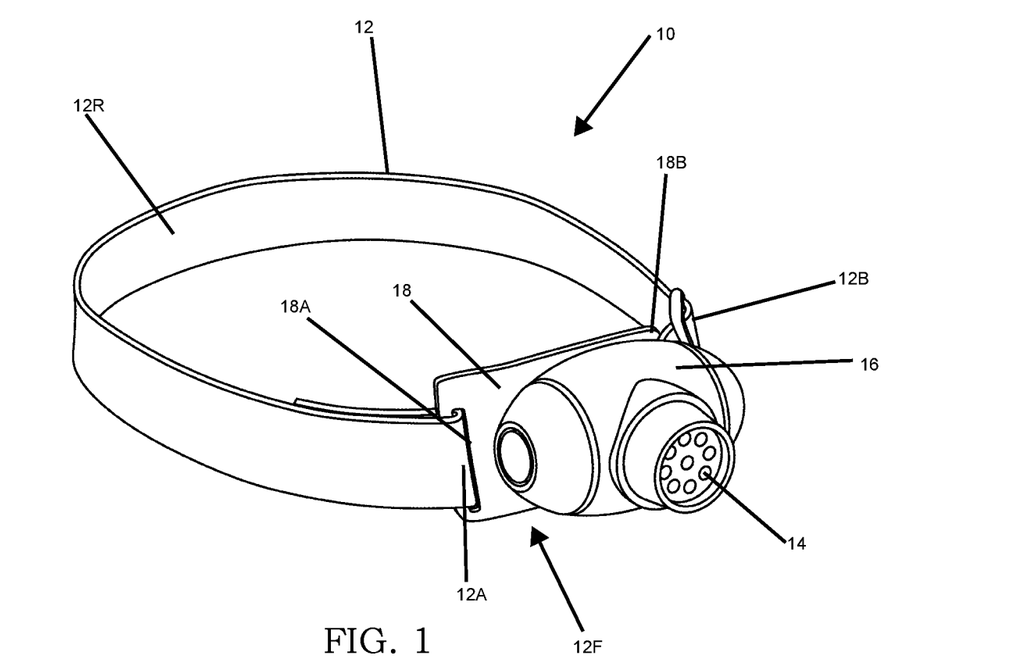
FIG. 1 shows a perspective view of the far-emitting ultraviolet headlamp of according to one embodiment of the present disclosed technology.
Figure 2:
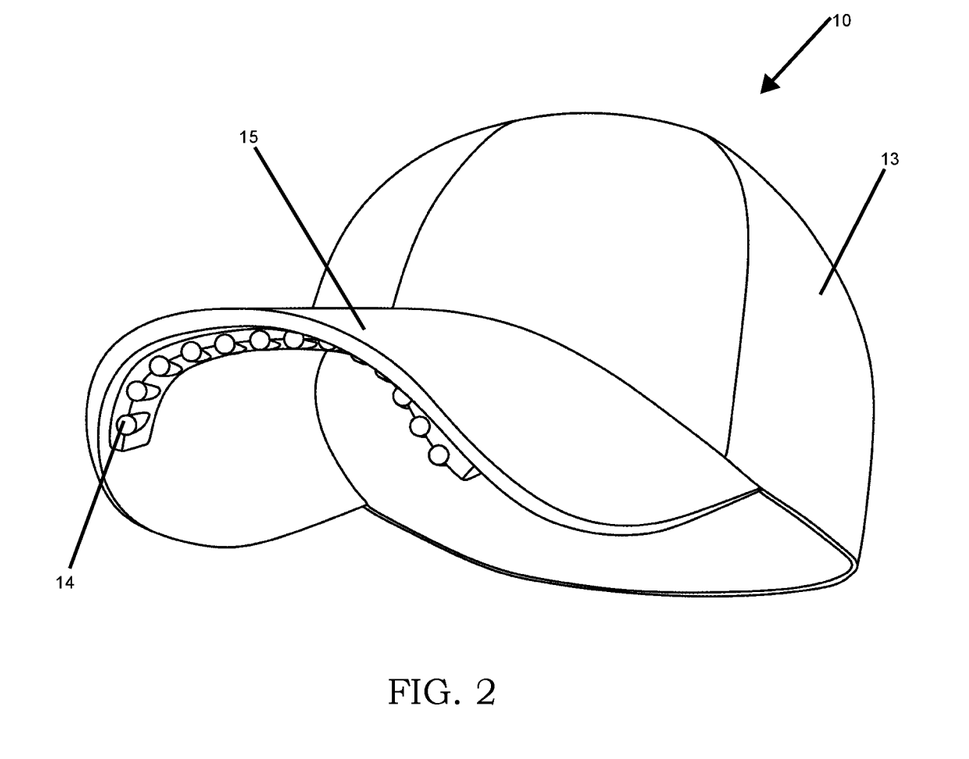
FIG. 2 shows a perspective view of the far-emitting ultraviolet headlamp of according to another embodiment of the present disclosed technology.
Figure 6:
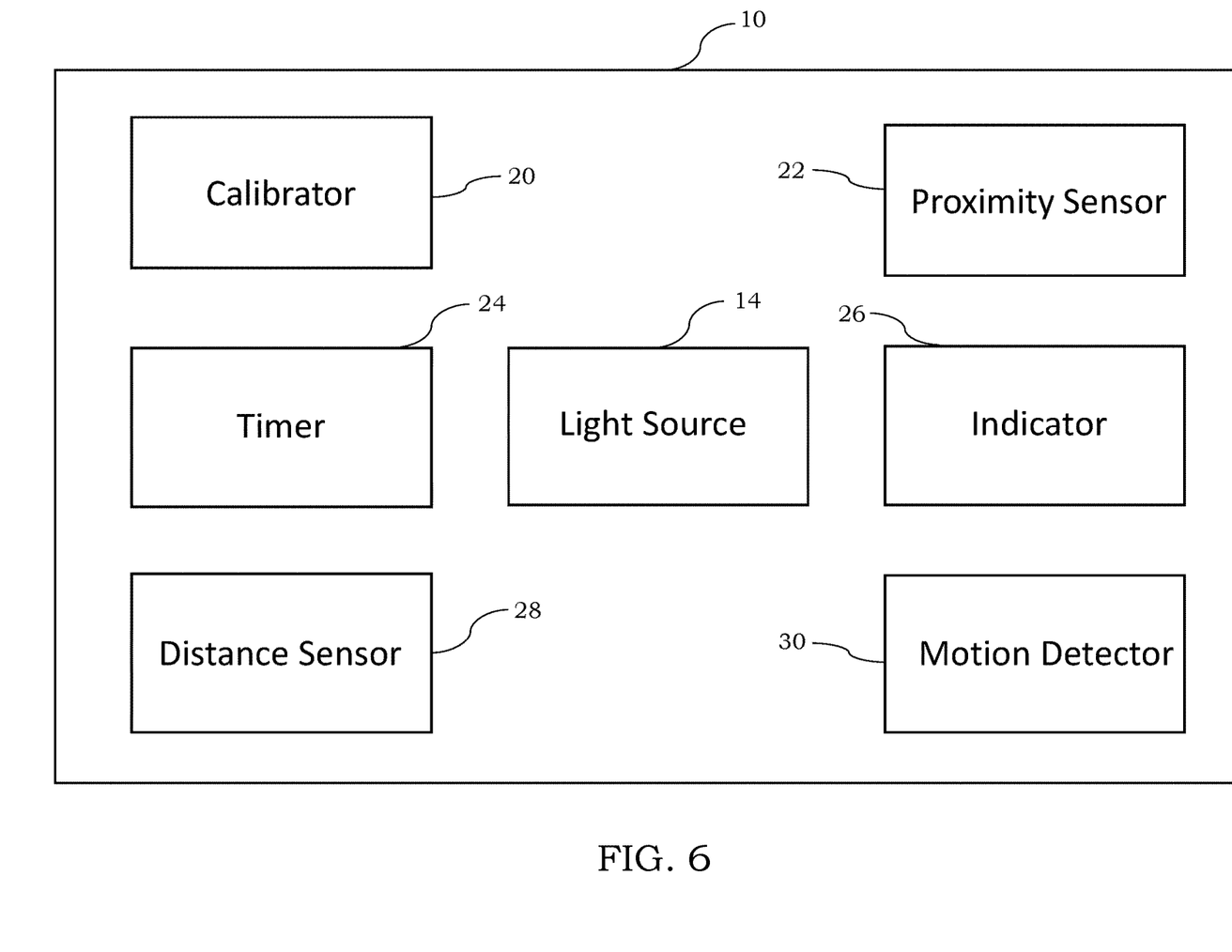
FIG. 6 shows a high-level block diagram of the far-emitting ultraviolet headlamp in use according to one embodiment of the present disclosed technology.

Referring now to FIG. 1, FIG. 2, and FIG. 6, simultaneously, FIG. 1 shows a perspective view of the far-emitting ultraviolet headlamp of according to one embodiment of the present disclosed technology. FIG. 2 shows a perspective view of the far-emitting ultraviolet headlamp of according to another embodiment of the present disclosed technology. FIG. 6 shows a high-level block diagram of the far-emitting ultraviolet headlamp in use according to one embodiment of the present disclosed technology. The far-emitting ultraviolet headlamp 10 comprises a head strap 12 for mounting circumferentially around a user's head, a light source 14 disposed the head strap 12, and an adjustment mechanism 16 coupled to the light source 14. The head strap 12 includes a circular strap having a first end 12A, a second end 12B opposite the first end 12A, a front end 12F, and a rear end 12R opposite the front end 12F. In embodiments, the headlamp 10 comprises a forehead pad 18 for abutting the user's forehead. The forehead pad 18 is disposed on the front end of the head strap 12 and includes a first side 18A and a second side 18B opposite the first side 18A. The first end 12A of the head strap 12 is adjustably coupled to the first side 18A of the forehead pad 18. The second end 12B of the head strap 12 is adjustably coupled to second side 18B of the head strap 12. In embodiments, the headlamp 10 comprises a hat 13 including a brim 15 lined with the light source 14.

The light source 14 is disposed on the front end 12Aa of the head strap 12. The light source 14 is oriented in a direction that is opposite the head strap 12 such that it emits lights away from the user's head when donned. The light source 14 is an ultraviolet light that emits ultraviolet light having a wavelength in the range of 200 to 280 nanometers. In some embodiments, the light source emits ultraviolet light at a wavelength ranging from 200 to 225 nanometers. In certain embodiments, the light source 14 emits a single wavelength of ultraviolet light at a wavelength of 222 nanometers. The light source 14 sanitizes surfaces in which it contacts by killing the RNA and the DNA of the microorganisms present on the surfaces with the ultraviolet light.

The adjustment mechanism 16 angles the light source with respect to the head strap 12 in the direction the user's eyes are looking such that the light emitted from the light source 14 makes contact with the surface being looked at. The adjustment mechanism 16 comprises a mechanical swivel which pivots the light source 14 along a vertical axis. In embodiments, the adjustment mechanism 16 comprises a calibrator 20 that angles the light source 14 into a specific position based on the position of the light source 14 with respect to the user's head, the length of the user's arm, and behaviometric information about the user. The behaviometric information may comprise data related to the frequency upon which the user lifts their hand to touch an object or surface and how far away the user lifts their hand when touching the object/surface. In this way, the calibrator aligns the light source 14 with the surfaces in which a user's desires to be sanitized, such that the light source 14 radiates ultraviolet light thereto. Further, the adjustment mechanism comprises, in embodiments of the disclosed technology, a power source there-within. The power source, such as a battery, is functionally and/or electrically connected to the light source 14 directly or by way of a switch and/or other devices shown in FIGS. 6 and/or 7. The battery, in some embodiments, is also or instead attached to the head strap 12, such as an a ventral side of the wearer.

For example, the calibrator 20 may angle the light source 14 via the adjustment mechanism 16 to shine the light source 14 toward an area where a person's hand is likely to be. This angle can be calibrated for the user based on the behaviometric information. In some embodiments, the angle and/or position in which the light source 14 is emanating its ultraviolet light can be calibrated based on data indicating an actual position of a hand (such as by way of a sensor on the person's hand or wrist giving position information such as height via infrared, angle of the arm, or a distance measuring system from a hat or the like). In this way, the light source 14 can point to a position of the user's hand before the hand reaches an object or surface to be touched.

The headlamp 10 may comprise a proximity sensor 22 coupled to the light source 14. The proximity sensor 22 senses the distance of a surface in the user's environment with respect to the light source 14. The proximity sensor 22 powers on the light source 14 when the proximity sensor 22 determines the user is within a predetermined distance away from the surface. For example, the predetermined distance may be between 0 and 10 feet in embodiments. In one embodiment, the predetermined distance may be between 1 and 2 feet. The proximity sensor 22 may be programmable such that predetermined distance may be set and changed by the user. The proximity sensor 22 may include an inductive proximity sensor, an optical proximity sensor, an infrared proximity sensor, a capacitive proximity sensor, a magnetic proximity sensor, or an ultrasonic proximity sensor.

The headlamp 10 may also comprise a timer 24 coupled to the light source 14. The timer 24 powers off the light source 14 when the light source 14 has contacted a surface after a predetermined amount of time. The timer 24 may be programmable such that predetermined amount of time may be set and changed by the user. The timer 24 may include a digital timer or mechanical timer.

In some embodiments, the headlamp 10 comprises an indicator 26 coupled to the light source 14 and the timer 24. The indicator 26 ques the user that the surface has been adequately sanitized after the predetermined amount of time has elapsed. The que notifies the user that the surface has been sanitized and is now safe to touch. The indicator 26 may include a visual indicator, such as a colored light positioned on the head strap 12 or a flashing light position on the head strap. For example, the indicator 26 may be visible light and can change in color, such as red for indicating stop and wait, and green indicating it's reasonably okay to proceed with the contact of the surface/object.

The indicator 26 may also include an audio indicator, such as an audio output including an alarm or pulsating noise such as a beep. The indicator 26 may also be an audio or video prompt that prompts the user where to point the light source 14. Since the ultraviolet light from the light source 14 can take time to kill all or substantially all of the microorganisms present on an object or surface, e.g. 3, 5, or 10 seconds, the indicator 26 can tell the user how long to wait before touching the surface. For example, this may be especially useful in hospital settings and for healthcare workers.

The amount of time necessary before it is safe for the user to touch the object/surface depends on, and can be calibrated to send prompts as a result of, distance of the object/surface from the headlamp 10, intensity of the ultraviolet light of the light source 14, focus of the light source 14, and the nature of the surface being cleansed with the ultraviolet light. In embodiments, the headlamp 10 comprises a distance sensor 28 to measure the distance from the headlamp 10 to an object/surface to be touched to aid in determining the time until an indication that the device can be touched is made. The distance sensor 28 may include an infrared sensor.

The headlamp 10 may also comprise a motion detector 30 coupled to the light source 14. The motion detector 30 detects motion adjacent to the light source 14. The motion detector 30 powers on the light source 14 when motion is detected proximate to the light source 14 and powers off the light source absent motion proximate to the light source 14. In this way, the motion detector 30 powers on the light source 14 when the user approaches a surface or another person and powers of the light source 14 to conserve battery when no surface or person is nearby. In one embodiment, the motion detector 30 powers off the light source 14 when motion is detected proximate to the light source 14 to power off the light source 14 when another person nearby. The motion detector 30 may comprise an infrared sensor, such as a passive infrared sensor, an ultrasonic sensor, a microwave sensor, a tomographic sensor, or any combination thereof. Note, the headlamp 10 may comprise any one of the proximity sensor 22, distance sensor 28, and motion sensor 30 to perform all of the functions of each.

Figure 3:
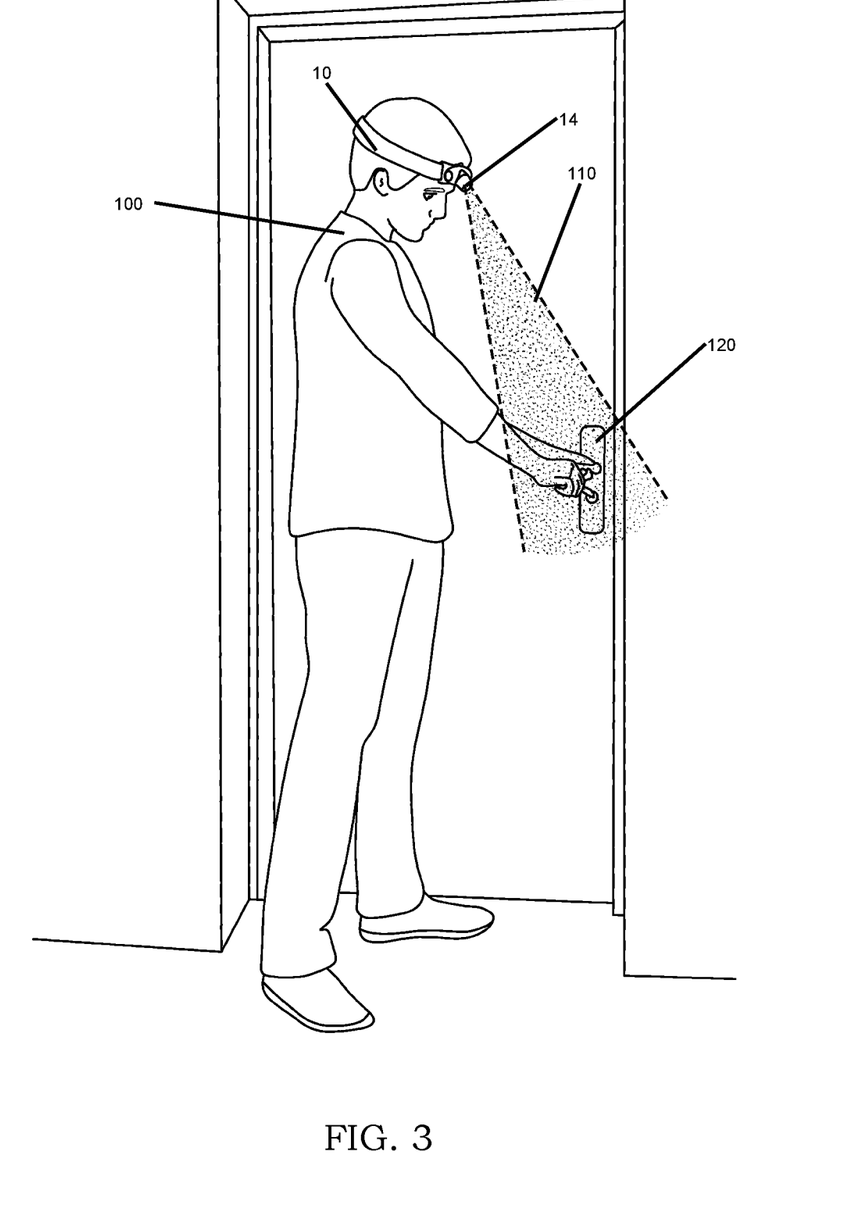
FIG. 3 shows a perspective view of the far-emitting ultraviolet headlamp in use according to one embodiment of the present disclosed technology.
Figure 4:
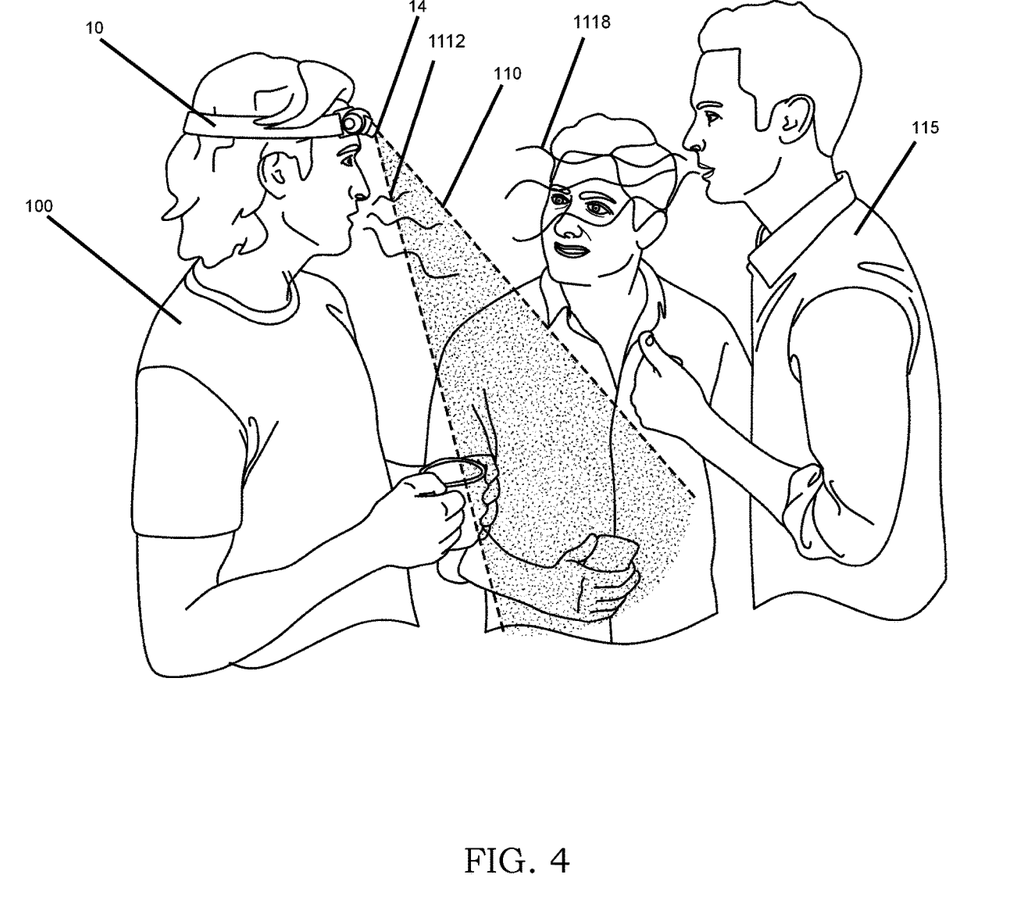
FIG. 4 shows a perspective view of the far-emitting ultraviolet headlamp in use according to one embodiment of the present disclosed technology.
Figure 5:
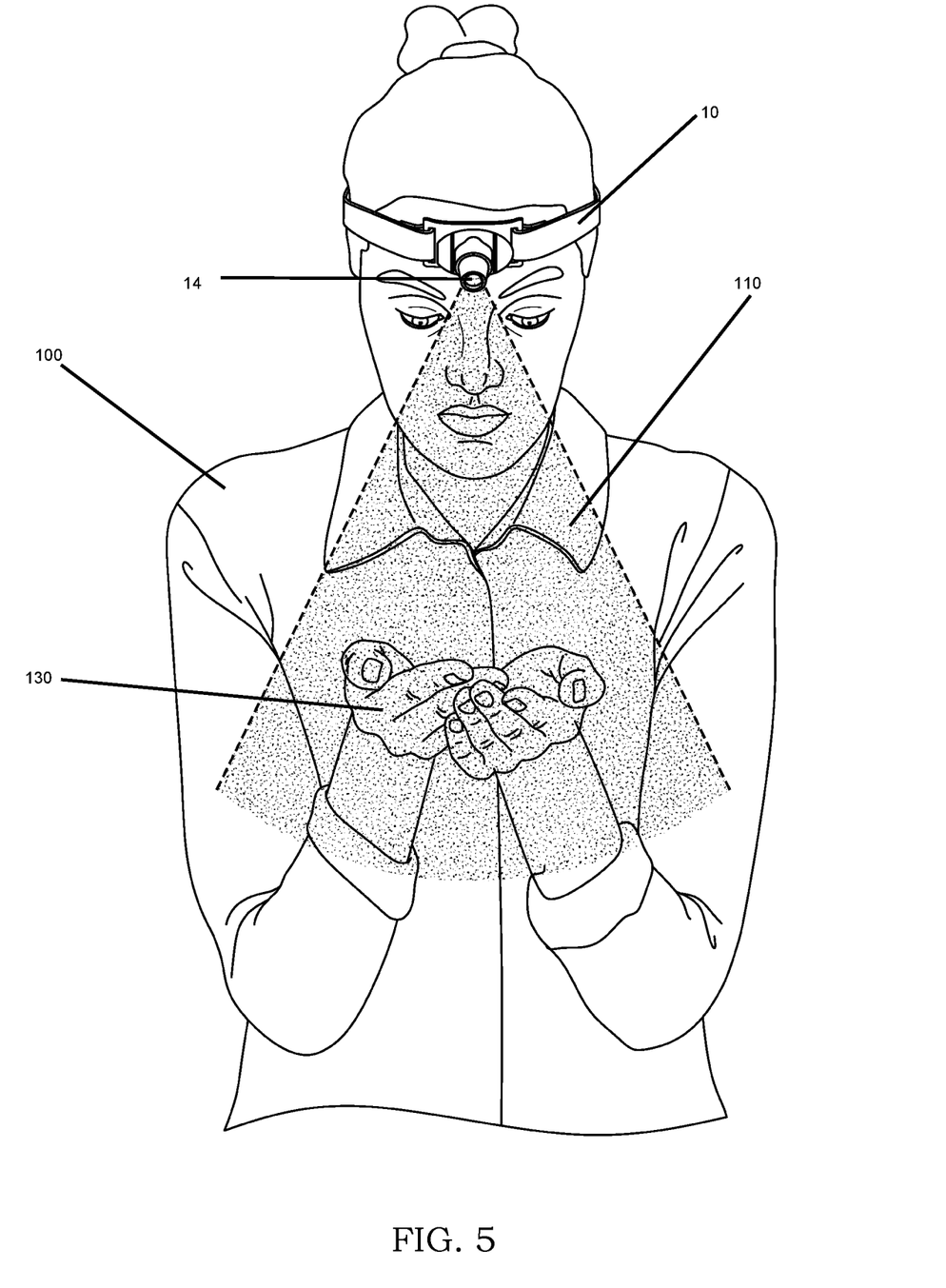
FIG. 5 shows a perspective view of the far-emitting ultraviolet headlamp in use according to one embodiment of the present disclosed technology.
Figure 7:
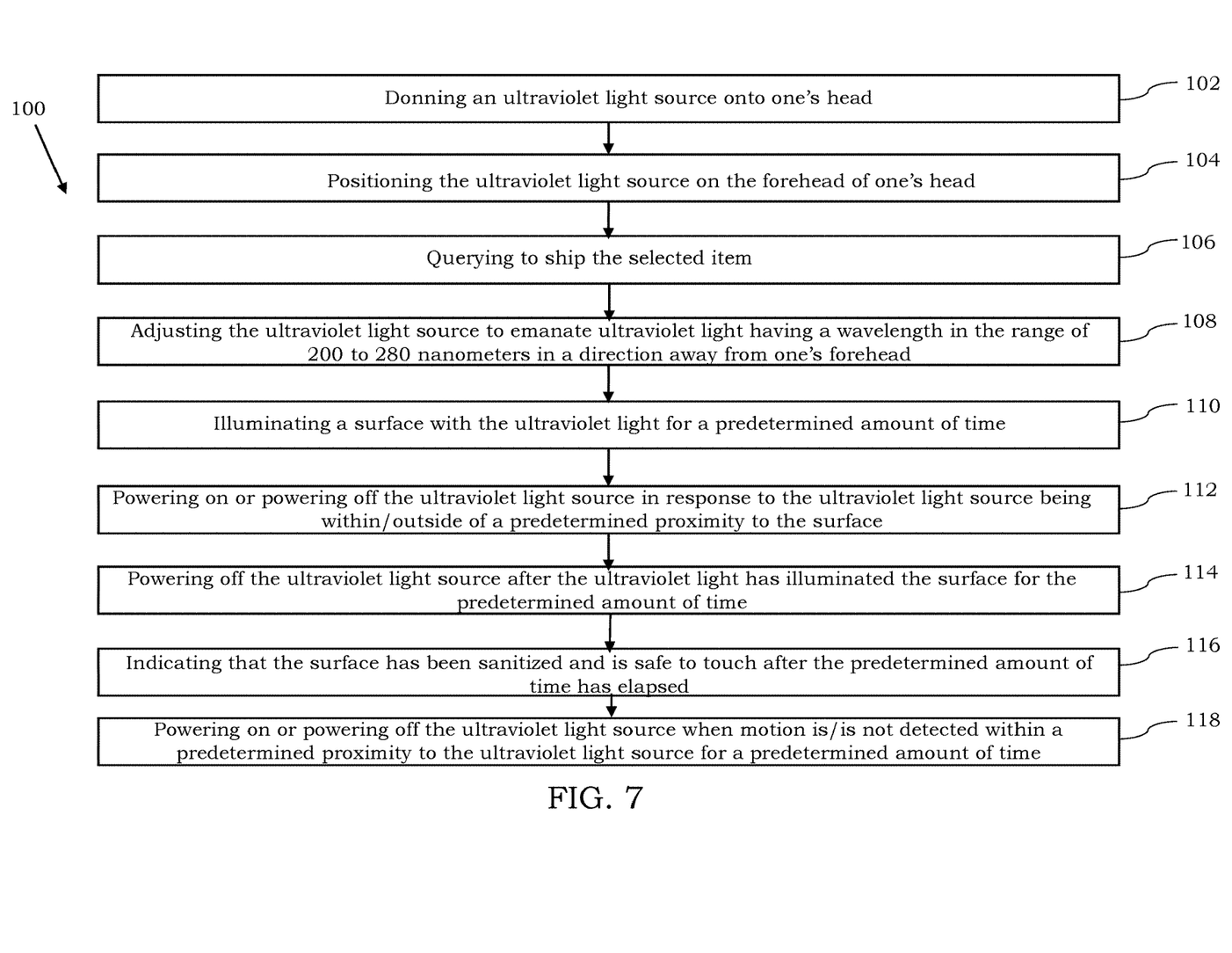
FIG. 7 shows a high-level flow chart of a method of killing microorganisms on a surface using the far-emitting ultraviolet headlamp according to one embodiment of present disclosed technology.

Referring now to FIG. 3, FIG. 4, FIG. 5, and FIG. 7, simultaneously, FIG. 3 shows a perspective view of the far-emitting ultraviolet headlamp in use according to one embodiment of the present disclosed technology. FIG. 4 shows a perspective view of the far-emitting ultraviolet headlamp in use according to one embodiment of the present disclosed technology. FIG. 5 shows a perspective view of the far-emitting ultraviolet headlamp in use according to one embodiment of the present disclosed technology. FIG. 7 shows a high-level flow chart of a method of killing microorganisms on a surface using the far-emitting ultraviolet headlamp according to one embodiment of present disclosed technology. The disclosed technology also provides a method 100 of killing microorganisms present on a surface with ultraviolet light disposed on a user's head. The method 100 comprises donning 102 an ultraviolet light source, such as the headlamp 10, onto the head, positioning 104 the ultraviolet light source on the forehead of the user's head, adjusting 106 the ultraviolet light source to emanate ultraviolet light having a wavelength in the range of 200 to 280 nanometers in a direction away from the user's forehead, directing 108 the ultraviolet light toward the surface, and illuminating 110 the surface with the ultraviolet light for a predetermined amount of time.

In some embodiments, the method 100 comprises powering on the ultraviolet light source in response to the ultraviolet light source being within a predetermined proximity to the surface and powering off the ultraviolet light source in response to the ultraviolet light source being outside of the predetermined proximity to the surface 112. In certain embodiments, the method 100 comprises powering off the ultraviolet light source after the ultraviolet light has illuminated the surface for the predetermined amount of time 114. In other embodiments, the method 100 comprises audially or visually indicating that the ultraviolet light has illuminated the surface for the predetermined amount of time to indicate when the surface has been sanitized and is safe to touch 116.

In alternative embodiments, the method 100 comprises powering on the ultraviolet light source when motion is detected within a predetermined proximity to the ultraviolet light source, and powering off the ultraviolet light source absent motion within the predetermined proximity to the ultraviolet light source for a predetermined amount of time 118. In embodiments, the illuminating step 110 comprises illuminating an area directly in front of the user at an angle in the range of 5 degrees to 45 degrees with respect to a vertical axis of the user.

For example, in one operation of the headlamp 10, the light source 14 is pointed downwards past the user's 100 face such that the ultraviolet light 110 emanating from the light source 14 kills any microorganisms emanating from the user's breath 1112 or to kill microorganisms present in air that is traveling towards the user's mouth, such as exhaled air 1118 from another person 115 that the user 100 is speaking to, as shown in FIG. 4.

In another operation of the headlamp 10, the light source 14 is oriented in front of the user 100 and diffused frontally or pointed towards a surface or object 120 upon which the user 100 is looking, such as a doorknob, such that any microorganisms present on the surface 120 are killed before the user 100 touches the surface 120, as show in FIG. 3. For example, in one embodiment of the disclosed technology, the direction of ultraviolet light 110 from the headlamp 10 is calibrated to point in the direction the user 100 is looking. The direction in which the ultraviolet light is oriented may be substantially perpendicular to the vertical axis of the user's 100 face and/or substantially parallel/tangential to the top of the user's 100 head. In this manner, the ultraviolet light 110 points in front of the user 100 and touches what they may be looking at. In another operation of the headlamp 10, the user 100 first looks at an object to be touched waits a few seconds, and then touches the sterilized/disinfected object.

In another operation of the headlamp 10, the user 100 can shine the ultraviolet light 110 on his or her hands 130 to kill any microorganisms present on the user's 100 hands 130 before the microorganisms reach the user's 100 mouth, nose, or eyes by way of his or her hands 130, as shown in FIG. 5. In this way, users may utilize the headlamp 10 to sterilize their hands before they touch their face, which is one of the primary modalities of infectious entry to the body.

Figure 8:
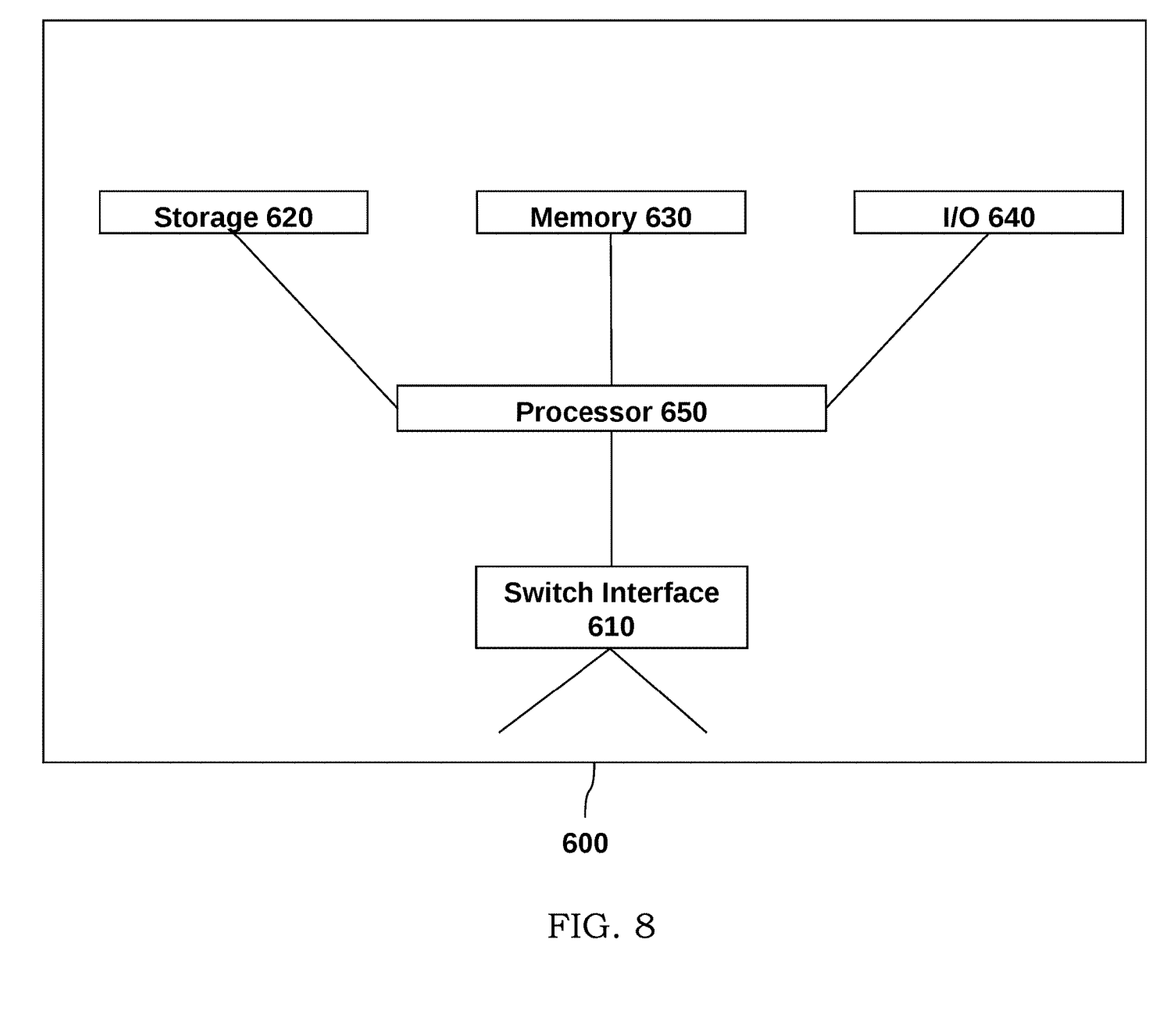
FIG. 8 shows a high-level block diagram of a device that may be used to carry out the disclosed technology according to one embodiment of the present disclosed technology.

FIG. 8 shows a high-level block diagram of a device that may be used to carry out the disclosed technology. Device 600 comprises a processor 650 that controls the overall operation of the computer by executing the device's program instructions which define such operation. The device's program instructions may be stored in a storage device 620 (e.g., magnetic disk, database) and loaded into memory 630, when execution of the console's program instructions is desired. Thus, the device's operation will be defined by the device's program instructions stored in memory 630 and/or storage 620, and the console will be controlled by processor 650 executing the console's program instructions. A device 600 also includes one, or a plurality of, input network interfaces for communicating with other devices via a network (e.g., the internet). The device 600 further includes an electrical input interface. A device 600 also includes one or more output network interfaces 610 for communicating with other devices. Device 600 also includes input/output 640, representing devices which allow for user interaction with a computer (e.g., display, keyboard, mouse, speakers, buttons, etc.). One skilled in the art will recognize that an implementation of an actual device will contain other components as well, and that FIG. 8 is a high-level representation of some of the components of such a device, for illustrative purposes. It should also be understood by one skilled in the art that the method and devices depicted in FIG. 1 through FIG. 7 may be implemented on a device such as is shown in FIG. 8.

Any device or step to a method described in this disclosure can comprise or consist of that which it is a part of, or the parts which make up the device or step. The term "and/or" is inclusive of the items which it joins linguistically and each item by itself.

For purposes of this disclosure, the term "substantially" is defined as "at least 95% of" the term which it modifies.

Any device or aspect of the technology can "comprise" or "consist of" the item it modifies, whether explicitly written as such or otherwise.

When the term "or" is used, it creates a group which has within either term being connected by the conjunction as well as both terms being connected by the conjunction.

While the disclosed technology has been disclosed with specific reference to the above embodiments, a person having ordinary skill in the art will recognize that changes can be made in form and detail without departing from the spirit and the scope of the disclosed technology. The described embodiments are to be considered in all respects only as illustrative and not restrictive. All changes that come within the meaning and range of equivalency of the claims are to be embraced within their scope. Combinations of any of the methods and apparatuses described hereinabove are also contemplated and within the scope of the invention.

What is claimed is:

1. A far-emitting ultraviolet headlamp for donning onto a user's head and sanitizing surfaces, comprising:
    a head strap for mounting circumferentially around a user's head, the head strap including a front end and a rear end opposite the front end;
    a light source disposed on the front end of the head strap, the light source emitting ultraviolet light having a wavelength in a range of 200 to 280 nanometers in a direction opposite the head strap, the ultraviolet light emitted from the light source sanitizing surfaces in which it contacts by killing all or substantially any RNA and any DNA of microorganisms present on the surface;
    a timer coupled to the light source, the timer configured to power off the light source when the light source has made contact with a surface after a predetermined amount of time; and
    an adjustment mechanism coupled to the light source, the adjustment mechanism angling the light source with respect to the head strap in a direction the user's eyes are looking such that the light emitted from the light source makes contact with the surface being looked at;
    wherein the predetermined amount of time is predetermined based on a combination of a distance of the surface from the light source, a intensity of the ultraviolet light being emitted from the light source, a focus of the light source, and a nature of the surface;
    wherein the adjustment mechanism comprises a calibrator configured to angle the light source into a specific position based on a position of a light source with respect to the user's head, a length of the user's arm, and behaviometric information about the user;

wherein the behaviometric information about the user comprise data related to a frequency upon which the user lifts their hand to touch an object and how far away the user lifts their hand when touching the object;
wherein the specific position in which the light source is directed by the calibrator is a position determined at least in part by a prediction made based on the behaviometric information.

2. The far-emitting ultraviolet headlamp of claim 1, further comprising a proximity sensor coupled to the light source, the proximity sensor sensing a distance of a surface in the user's environment with respect to the light source, the proximity sensor powering on the light source when the proximity sensor determines the user is within a predetermined distance away from the surface.

3. The far-emitting ultraviolet headlamp of claim 2, wherein the predetermined distance from the surface, as well as the specific predetermined time to be used based on the combination of the distance of the surface from the light source, the intensity of the ultraviolet light being emitted from the light source, the focus of the light source, and the nature of the surface are reprogrammable by a user.

4. The far-emitting ultraviolet headlamp of claim 3, further comprising a visual indicator coupled to the light source and the timer, the visual indicator queuing the user that the surface has been adequately sanitized after the predetermined amount of time has elapsed to notify the user that the surface is safe to touch.

5. The far-emitting ultraviolet headlamp of claim 4, wherein the visual indicator is a colored light positioned on the head strap.

6. The far-emitting ultraviolet headlamp of claim 3, further comprising an audio indicator coupled to the light source and the timer, the audio indicator queuing the user that the surface has been adequately sanitized after the predetermined amount of time has elapsed to notify the user that the surface is safe to touch.

7. The far-emitting ultraviolet headlamp of claim 4, further comprising a motion detector coupled to the light source, the motion detector detecting motion adjacent to the light source, the motion detector powering on the light source when motion is detected proximate to the light source and powering off the light source absent motion proximate to the light source.

8. The far-emitting ultraviolet headlamp of claim 1, wherein the adjustment mechanism comprises a mechanical swivel which pivots the light source along a vertical axis;
wherein the light source is manually adjustable.

9. The far-emitting ultraviolet headlamp of claim 1, wherein the range of wavelengths emitted from the light source is automatically adjustable to a specific range such that the wavelength is sufficient to sanitize the surface and is insufficient to damage the surface being sanitized.

10. The far-emitting ultraviolet headlamp of claim 1, wherein the predetermined amount of time after which the timer powers off the light source changes when one or more of the distance from the surface to the light source, the intensity of the ultraviolet light being emitted from the light source, the focus of the light source, and the nature of the surface being sanitized change.

11. The far-emitting ultraviolet headlamp of claim 1, wherein the light source emits ultraviolet light at a wavelength ranging from 200 to 225 nanometers.

12. The far-emitting ultraviolet headlamp of claim 7, wherein the light source emits a single wavelength of ultraviolet light at a wavelength of 222 nanometers.

13. The far-emitting ultraviolet headlamp of claim 1, further comprising a forehead pad for abutting the user's forehead, the forehead pad disposed on the front end of the head strap, the forehead pad including a first side and a second side opposite the first side;
wherein a width between the first side and a second side, and a material of the forehead pad, is such that the forehead pad is sufficient to cushion against movement of the headlamp.

14. The far-emitting ultraviolet headlamp of claim 13, wherein the head strap includes a first end and a second end opposite the first end, the first end adjustably coupled to the first side of the forehead pad, the second end adjustably coupled to the second side of the head strap.

15. A method of simultaneously killing microorganisms present on a plurality of surfaces comprising at least two surfaces with an ultraviolet light disposed on a user's head, comprising:
donning an ultraviolet light source onto the head;
positioning the ultraviolet light source on a forehead of the user's head;
adjusting the ultraviolet light source to emanate ultraviolet light having a wavelength in a range of 200 to 280 nanometers in a direction away from the user's forehead;
directing the ultraviolet light toward the at least two surfaces; and
illuminating each of the at least two surfaces with the ultraviolet light for a predetermined amount of time;
wherein the predetermined amount of time is predetermined based on a combination of distances of each of the at least two surfaces from the light source, the intensity range of the ultraviolet light being emitted from the light source, a focus of the light source, and natures of the at least two surfaces.

16. The method of claim 15, further comprising:
powering on the ultraviolet light source in response to the ultraviolet light source being within a predetermined proximity to at least one of the at least two surfaces; and
powering off the ultraviolet light source in response to the ultraviolet light source being outside of the predetermined proximity to all of the at least two surfaces;
wherein the predetermined proximity is a range of distances between the light source and any surface of the at least two surfaces and being outside of the predetermined proximity comprises being closer to the light source than a smallest number of the range of the predetermined proximity range or being further from the light source than a largest number of the range of the predetermined proximity range.

17. The method of claim 16, further comprising powering off the ultraviolet light source after the ultraviolet light has illuminated the at least two surfaces for the predetermined amount of time.

18. The method of claim 17, further comprising audially or visually indicating that the ultraviolet light has illuminated the at least two surfaces for the predetermined amount of time to indicate when the at least two surfaces have been sanitized and are safe to touch.

19. The method of claim 18, further comprising:
powering on the ultraviolet light source when motion is detected within a predetermined proximity to the ultraviolet light source; and
powering off the ultraviolet light source absent motion within the predetermined proximity to the ultraviolet light source for a predetermined amount of time.

20. The method of claim 19, further comprising illuminating an area directly in front of the user at an angle in a range of 5 degrees to 45 degrees with respect to a vertical axis of the user.

\* \* \* \* \*